(12) United States Patent
Walsh et al.

(10) Patent No.: US 7,429,464 B2
(45) Date of Patent: *Sep. 30, 2008

(54) METHODS FOR DETECTING BACTERIAL PATHOGENS

(75) Inventors: John D. Walsh, Durham, NC (US); Jones M. Hyman, Wake Forest, NC (US)

(73) Assignee: bioMerieux, Inc., Durham, NC (US)

( * ) Notice: Subject to any disclaimer, the term of this patent is extended or adjusted under 35 U.S.C. 154(b) by 84 days.

This patent is subject to a terminal disclaimer.

(21) Appl. No.: 11/006,025

(22) Filed: Dec. 7, 2004

(65) Prior Publication Data

US 2005/0244918 A1   Nov. 3, 2005

Related U.S. Application Data

(60) Provisional application No. 60/572,824, filed on May 20, 2004, provisional application No. 60/527,926, filed on Dec. 9, 2003.

(51) Int. Cl.
C12Q 1/14 (2006.01)
C12Q 1/04 (2006.01)

(52) U.S. Cl. .......................... 435/36; 435/34
(58) Field of Classification Search ........................ None
See application file for complete search history.

(56) References Cited

U.S. PATENT DOCUMENTS

| | | | |
|---|---|---|---|
| 4,362,531 A * | 12/1982 | de Steenwinkel et al. ... | 436/512 |
| 4,617,264 A * | 10/1986 | Whiteley et al. ........... | 435/7.36 |
| 4,632,902 A | 12/1986 | Waters et al. | |
| 5,496,706 A | 3/1996 | Kuusela et al. | |
| 5,989,821 A | 11/1999 | Goh et al. | |
| 6,156,507 A | 12/2000 | Hiramatsu et al. | |
| 6,156,524 A | 12/2000 | Fournier | |
| 6,312,903 B1 | 11/2001 | Jannes et al. | |
| 6,340,571 B1 | 1/2002 | Merlin et al. | |
| 6,649,414 B1 * | 11/2003 | Chandler et al. ............... | 436/63 |
| 2001/0044125 A1 * | 11/2001 | Ono et al. ................... | 435/7.32 |
| 2002/0055101 A1 | 5/2002 | Bergeron et al. | |
| 2002/0086289 A1 | 7/2002 | Straus | |
| 2002/0147317 A1 | 10/2002 | Bentsen et al. | |
| 2003/0054436 A1 | 3/2003 | Kunsch et al. | |

FOREIGN PATENT DOCUMENTS

| | | |
|---|---|---|
| EP | 0323331 | 7/1989 |
| WO | WO 98/32874 | 7/1998 |
| WO | WO 02/079486 | 10/2002 |
| WO | WO 02/082086 | 10/2002 |

OTHER PUBLICATIONS

Essers L and Radebold K. (Nov. 1980) Rapid and reliable identification of *Staphylococcus aureus* by a latex agglutination test. J Clin Microbiol, vol. 12, No. 5, pp. 641-643.*

Simsonson et al (Dec. 1986) Rapid serological identification of *Vibrio vulnificus* by anti-H coagglutination. Appl Environ Microbiol, vol. 52, No. 6, pp. 1299-1304.*

Papasian, Christopher J. et al., "Evaluation of a Rapid Slide Agglutination Test for Identification of *Staphylococcus aureus*," Diagnostic Microbiology and Infectious Disease, vol. 33, No. 3, pp. 201-203 (Mar. 1999).

* cited by examiner

*Primary Examiner*—Lisa J Hobbs
(74) *Attorney, Agent, or Firm*—Myers Bigel Sibley & Sajovec, P.A.

(57) ABSTRACT

The present invention provides for methods for detecting bacterial pathogens in a sample. A preferred method includes the steps of: suspending a sample comprising a medium and microorganisms, the microorganisms suspected of comprising bacterial pathogens; mixing the sample, an adsorbent and a first solution in a vessel; separating the adsorbent and the microorganisms from the medium and the bulk of the first solution and removing the medium and the bulk of the first solution from the vessel; adding a second solution to the vessel to resuspend the adsorbent and the microorganisms; and detecting agglutination of the adsorbent wherein the agglutination of the adsorbent signifies bacterial pathogens are present in the sample.

17 Claims, 1 Drawing Sheet

METHODS FOR DETECTING BACTERIAL PATHOGENS

CROSS-REFERENCE TO RELATED APPLICATIONS

This application claims the benefit of U.S. Provisional Patent Application No. 60/527,926 filed on Dec. 9, 2003 and U.S. Provisional Patent Application No. 60/572,824 filed on May 20, 2004.

FIELD OF THE INVENTION

The present invention relates to methods for the identification of bacterial pathogens. More particularly, the present invention relates to the identification of Staphylococci such as *Staphylococcus aureus* and Enterococci such as *Enterococcus faecalis* in samples.

BACKGROUND OF THE INVENTION

The genus *Staphylococcus* includes at least 20 distinct species. (For a review, see Novick, R. P., The *Staphylococcus* as a Molecular Genetic System, Chapter 1, pgs. 1-37 in MOLECULAR BIOLOGY OF THE STAPHYLOCOCCI, R. Novick, Ed., VCH Publishers, New York (1990)). The species differ from one another by 80% or more, by hybridization kinetics, whereas strains within a species are at least 90% identical by the same measure.

The species *Staphylococcus aureus* is a gram-positive, facultatively aerobic, clump-forming cocci considered among the most virulent species of the genus.

*Staphylococcus aureus* is a ubiquitous pathogen. (See, for instance, Mims et al., MEDICAL MICROBIOLOGY, Mosby-Year Book Europe Limited, London, UK (1993)). It is an etiological agent of a variety of conditions, ranging in severity from mild to fatal. A few of the more common conditions caused by *S. aureus* infection are burns, cellulitis, eyelid infections, food poisoning, joint infections, neonatal conjunctivitis, osteomyelitis, skin infections, surgical wound infection, scalded skin syndrome and toxic shock syndrome. *Staphylococcus aureus* also causes more serious illnesses such as pneumonia, meningitis and bacteremia.

When introduced in food, *Staphylococcus aureus* may produce one or more *Staphylococcal* enterotoxins. If ingested, heat stable *Staphylococcal* enterotoxins may produce symptoms of food poisoning and a range of other diseases.

*Staphylococcus aureus* possesses a protective cell wall which comprises a cross-linked peptidoglycan layer. The cell wall is resistant to phagocytosis which is thought to be due, in part, to the production of Protein A on the cell surface. *Staphylococcus aureus* also produces hemolytic toxin which may damage blood cells and immune cells.

Accordingly, it is readily apparent that it is important that bacterial pathogens such as *Staphylococcus aureus* can be identified in samples. To that end, several methods have been disclosed for detecting *Staphylococcus aureus*. For example, U.S. Pat. No. 5,496,706 discloses a method for detecting *Staphylococcus aureus* in a sample. The method uses anti-MRSA-230 antibodies to detect *Staphylococcus aureus* by visible agglutination means. This method, though, can be quite expensive.

Many laboratories perform a slide coagulase test as a rapid, inexpensive method for presumptive identification of *S. aureus*. This test relies on the observation of clumping of a heavy suspension of *S. aureus* cells in the presence of a drop of plasma placed on a slide. The clumping is mediated by the binding of fibrinogen with a specific receptor of the surface of the bacterium, termed clumping factor. However, a slide coagulase test has significant drawbacks. For example, 10 to 15% of *S. aureus* isolates yield false negative results requiring all negatives to be confirmed in a tube coagulase test. A tube coagulase test is another commonly used method for identifying *S. aureus*. This method, though, requires an incubation period of 4 to 24 hours.

In addition, rapid cycle, real-time PCR methods can provide results in thirty (30) minutes and in situ probe hybridization methods such as FISH can provide results within ninety (90) minutes. However, these methods are expensive and/or labor intensive.

Further, testing of positive blood culture broth samples using latex tests has not been recommended due to poor assay sensitivity and specificity. See McDonald, C. L. et al., J. Clin. Microbiol. 33:50-52 (1995) and Spears, D. J. et al., J. Clin. Microbiol. 36:1032-1034 (1998). Thus, there is a need in the art for a rapid, accurate and inexpensive means for detecting and identifying bacterial pathogens including *Staphylococcus aureus*.

SUMMARY OF THE INVENTION

The present invention provides for a method for detecting bacterial pathogens in a sample which is rapid, accurate and less expensive than the methods of the prior art. The method comprises the steps of:
(a) suspending a sample comprising a medium and microorganisms, the microorganisms suspected of comprising bacterial pathogens;
(b) mixing the sample, an adsorbent and a first solution in a vessel;
(c) separating the adsorbent and the microorganisms from the medium and the bulk of the first solution and removing the medium and the bulk of the first solution from the vessel;
(d) adding a second solution to the vessel to resuspend the adsorbent and the microorganisms; and
(e) detecting agglutination of the adsorbent wherein the agglutination of the adsorbent signifies bacterial pathogens are present in the sample.

The present invention also provides for another method for detecting bacterial pathogens in a sample. This method comprises the steps of:
(a) suspending a sample comprising a medium, an adsorbent and microorganisms, the microorganisms suspected of comprising bacterial pathogens;
(b) mixing the sample and a first solution in a vessel;
(c) separating the adsorbent and the microorganisms from the medium and the bulk of the first solution and removing the medium and the bulk of the first solution from the vessel;
(d) adding a second solution to the vessel to resuspend the adsorbent and the microorganisms; and
(e) detecting agglutination of the adsorbent wherein the agglutination of the adsorbent signifies bacterial pathogens are present in the sample.

The present invention also provides a method for detecting *Staphylococcus aureus* in a sample. This method comprises the steps of:
(a) suspending a sample comprising a medium and microorganisms, the microorganisms suspected of comprising *Staphylococcus aureus;*
(b) mixing the sample, an adsorbent and a first solution in a vessel, the adsorbent comprising activated charcoal;

(c) separating the adsorbent and the microorganisms from the medium and the bulk of the first solution and removing the medium and the bulk of the first solution from the vessel;
(d) adding a second solution to the vessel to resuspend the adsorbent and the microorganisms; and
(e) detecting agglutination of the adsorbent wherein the agglutination of the adsorbent signifies *Staphylococcus aureus* is present in the sample;

wherein plasma, serum, blood or a blood component is mixed with the sample, the adsorbent and the first solution in step (b) and separated and removed from the vessel in step (c) with the medium and the bulk of the first solution.

The present invention also provides for another method for detecting *Staphylococcus aureus* in a sample. This method comprises the steps of:
(a) suspending a sample comprising a medium, an adsorbent and microorganisms, the microorganisms suspected of comprising *Staphylococcus aureus* and the adsorbent comprising activated charcoal;
(b) mixing the sample and a first solution in a vessel;
(c) separating the adsorbent and the microorganisms from the medium and the bulk of the first solution and removing the medium and the bulk of the first solution from the vessel;
(d) adding a second solution to the vessel to resuspend the adsorbent and the microorganisms; and
(e) detecting agglutination of the adsorbent wherein the agglutination of the adsorbent signifies *Staphylococcus aureus* is present in the sample; wherein plasma, serum, blood or a blood component is mixed with the sample and the first solution in step (b) and separated and removed from the vessel in step (c) with the medium and the bulk of the first solution.

The above-described methods provide a definitive result within fifteen (15) minutes allowing the attending physician to be notified of the identification of the bacterial pathogens.

DETAILED DESCRIPTION OF THE INVENTION

Figure 1:
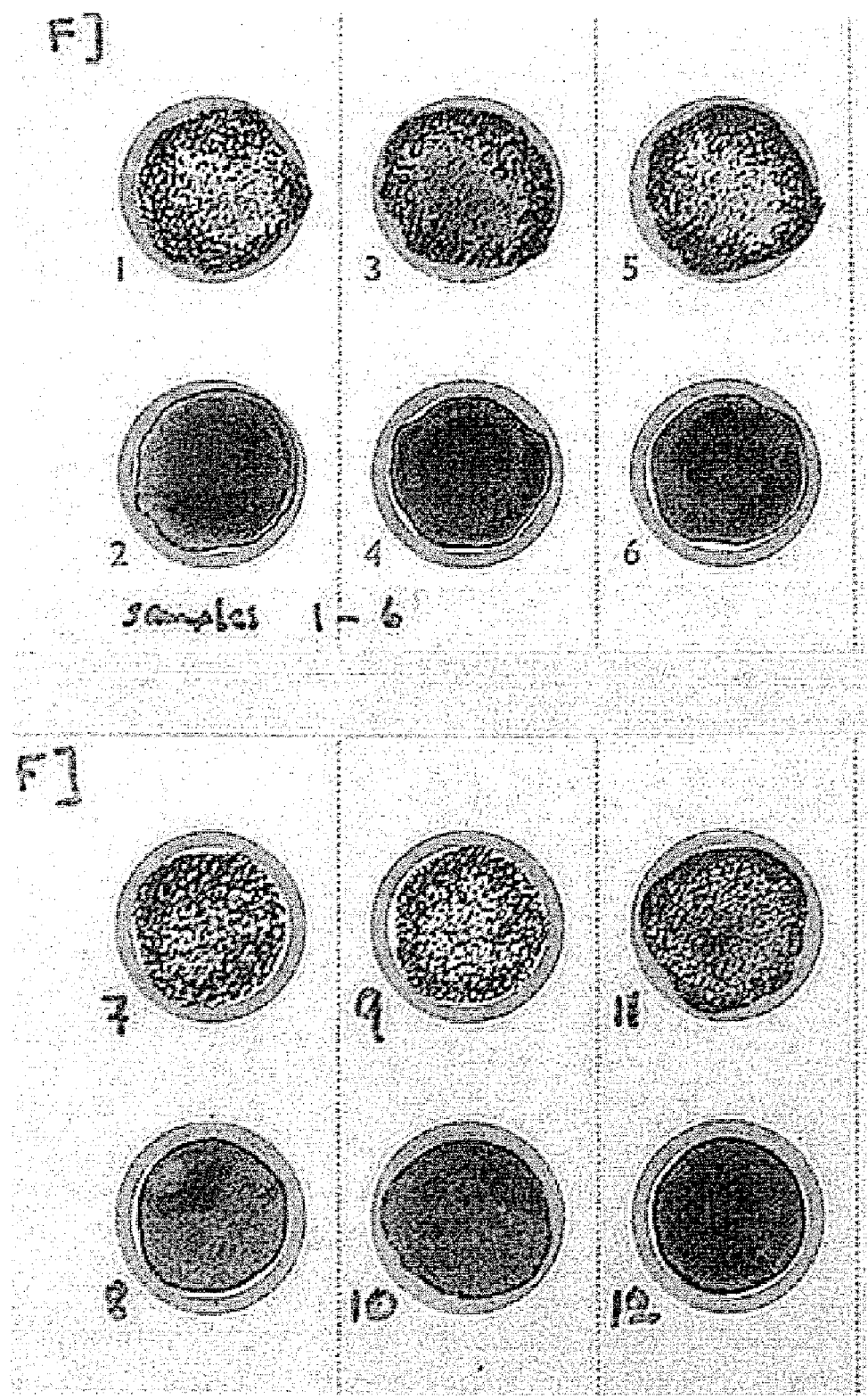
FIG. 1 shows the agglutination pattern of several samples tested according to a method of the present invention.

As stated above, the present invention provides for a method for detecting bacterial pathogens in a sample comprising the steps of:
(a) suspending a sample comprising a medium and microorganisms, the microorganisms suspected of comprising bacterial pathogens;
(b) mixing the sample, an adsorbent and a first solution in a vessel;
(c) separating the adsorbent and the microorganisms from the medium and the bulk of the first solution and removing the medium and the bulk of the first solution from the vessel;
(d) adding a second solution to the vessel to resuspend the adsorbent and the microorganisms; and
(e) detecting agglutination of the adsorbent wherein the agglutination of the adsorbent signifies bacterial pathogens are present in the sample.

Bacterial pathogens that can be detected by this method include *Staphylococcus aureus* and *Enterococcus faecalis*.

Samples that can be used in this method of the present invention can be obtained from any source including, but not limited to, blood, blood products, tissue, ascites, culture media, body fluids, skin, pus, uro-genital specimens, feces, foodstuffs, beverages, cosmetic products, pharmaceutical products, healthcare products, surfaces such as floors and tables, and airborne particles such as pollen and dust. The sample will be one that is suspected of having microorganisms. The sample may already have been tested for the presence of microorganisms and have tested positive for microorganisms. The sample will require the addition of a medium prior to step (a) if it does not include any medium and the medium is preferably a growth medium. The amount of medium that must be added to the sample will be dependent upon the estimated number of microorganisms in the sample and could easily be ascertained by one skilled in the art.

Plasma, serum, blood or a blood component is preferably mixed with the sample, the adsorbent and the first solution in step (b). If plasma, serum, blood or a blood component is mixed with the sample, the adsorbent and the first solution, the bulk of the plasma, serum, blood or a blood component is separated along with the medium and the bulk of the first solution from the adsorbent and the microorganisms and removed from the vessel during step (c). The sample, though, may be obtained from a source such as blood, blood products, tissue, body fluids, skin, pus, etc., and therefore already include plasma, serum, blood or a blood component. In such instances, the bulk of the plasma, serum, blood or a blood component is separated along with the medium and the bulk of the first solution from the adsorbent and the microorganisms during step (c).

The sample as provided in step (a) is suspended and this can be accomplished by gently shaking the container or vessel containing the sample. Step (b) provides that the sample, adsorbent and first solution are mixed in a vessel and this can be accomplished by briefly vortexing the vessel. The vessel is preferably a conical tube.

The adsorbent is selected from the group consisting of aluminum oxide, colloidal native hydrated aluminum silicates, crystalline hydrated alkali-aluminum silicates, silica, siliceous frustules, fragments of various species of diatoms, amorphous carbon, ion exchange resins, non-functional polymeric resin adsorbents, polystyrene resin cross-linked with divinyl benzene, activated charcoal, charcoal bound to fibers, fuller's earth bound to fibers, charcoal bound to fuller's earth and combinations thereof. Preferably, the adsorbent comprises activated charcoal.

Further, the amount of adsorbent that can be mixed with the sample and first solution in step (b) is from about 5 to about 150 mg. Preferably, the amount of adsorbent mixed with the sample and first solution in step (b) is from about 25 to about 50 mg. More preferably, the adsorbent comprises activated charcoal and the amount of activated charcoal mixed with the sample and first solution in step (b) is about 0.5 mL of an autoclaved suspension of 6.5% w/v activated charcoal.

The amount of sample that can be mixed with the adsorbent and first solution in step (b) is from about 0.1 to about 10 mL. Preferably, the amount of sample mixed with the adsorbent and first solution in step (b) is about 2.5 mL.

The amount of the first solution that can be mixed with the sample and the adsorbent in step (b) is from about 0.1 to about 10 mL. The first solution preferably comprises an alkaline reagent. Alkaline reagents that can be used include, but are not limited to, ethanolamine, tri-sodium phosphate, sodium hydroxide and potassium hydroxide. The first solution can also comprise a detergent. Most preferably, the first solution comprises an alkaline reagent, a detergent and a chelating agent. Detergents that can be used with the present invention include, but are not limited to, cholic acid, deoxycholic acid, digitonin, n-dodecyl-.beta.-D-maltoside, glycodeoxycholic acid, n-lauroylsarcosine, lauryl sulfate, Triton X-100, saponin, polyoxyethylene sorbitan monooleate, polyethylene glycol P-1,1,3,3-tetramethylbutylphenyl ether and polyoxyethylene derivatives of fatty acids. Chelating agents that can be used with the present invention include, but are not limited to, EGTA and EDTA.

In a preferred embodiment, the first solution comprises sodium hydroxide, Triton X-100 and EDTA. More particularly, the first solution comprises 0.2 N sodium hydroxide, 1.0% Triton X-100 and 1 mM EDTA. The amount of this first solution that can be mixed with the sample and the adsorbent in step (b) is from about 0.1 to about 10 mL. Preferably, the amount of this first solution mixed with the sample and the adsorbent in step (b) is about 2.5 mL.

The above method provides for separating the adsorbent and the microorganisms from the medium and the bulk of the first solution and removing the medium and the bulk of the first solution from the vessel. Preferably, the adsorbent and the microorganisms can be separated from the medium and the bulk of the first solution by centrifugation or filtration. Most preferably, the adsorbent and the microorganisms are separated from the medium and the bulk of the first solution by centrifugation for ten (10) minutes at ≧1,000 G to pellet the adsorbent and the microorganisms. Preferably, the medium is a growth medium.

Step (d) of the above method provides for adding a second solution to the vessel to resuspend the adsorbent and the microorganisms. After the second solution is added to the vessel, the vessel should be vortexed.

The amount of the second solution that can be added to the vessel in step (d) is from about 0.05 mL to about 5 mL. Preferably, the second solution comprises an acidic solution and/or a buffer such as Tris, HEPES, MOPS and phosphate. Buffers that can be used with the present invention have a pKa in the range of from about 5.0 to about 9.0. More preferably, buffers that can be used with the present invention have a pKa in the range of from about 6.0 to about 8.0.

Preferably, the second solution comprises a detergent and/or a salt. Detergents that can be used with the present invention include, but are not limited to, cholic acid, deoxycholic acid, digitonin, n-dodecyl-.beta.-D-maltoside, glycodeoxycholic acid, n-lauroylsarcosine, Triton X-100, lauryl sulfate, saponin, polyoxyethylene sorbitan monooleate, polyethylene glycol P-1,1,3,3-tetramethylbutylphenyl ether and polyoxyethylene derivatives of fatty acids. Salts that can be used with present invention include, but are not limited to, potassium chloride, sodium chloride, magnesium chloride, magnesium sulfate and calcium chloride.

In a preferred embodiment, the second solution comprises Tris, sodium chloride and Tween 80. More particularly, the second solution comprises 0.1 M Tris (pH 7.2), 0.15 M sodium chloride and 0.5% Tween 80. The amount of this second solution that can be added to the vessel in step (d) is from about 0.05 mL to about 5 mL. Preferably, the amount of this second solution added to the vessel in step (d) is about 1.0 mL.

Step (e) of the above method provides for detecting agglutination of the adsorbent which signifies bacterial pathogens are present in the sample. This can be accomplished in several ways such as light scattering methods, sedimentation methods, gently tilting the vessel and examining the vessel for clumping of the adsorbent, placing a drop of the adsorbent onto a glass slide and rocking the slide for up to 15 seconds or mixing it with a disposable loop, or placing 25 to 50 μL of the suspension onto a latex test card circle and mixing it with a disposable loop. Rapid, visible agglutination of the adsorbent is presumptive positive identification of bacterial pathogens.

The present invention also provides for another method for detecting bacterial pathogens in a sample. This method comprises the steps of:

(a) suspending a sample comprising a medium, an adsorbent and microorganisms, the microorganisms suspected of comprising bacterial pathogens;

(b) mixing the sample and a first solution in a vessel;

(c) separating the adsorbent and the microorganisms from the medium and the bulk of the first solution and removing the medium and the bulk of the first solution from the vessel;

(d) adding a second solution to the vessel to resuspend the adsorbent and the microorganisms; and (e) detecting agglutination of the adsorbent wherein the agglutination of the adsorbent signifies bacterial pathogens are present in the sample.

Bacterial pathogens that can be detected by this method include *Staphylococcus aureus* and *Enterococcus faecalis*.

Samples that can be used in this method of the present invention can be obtained from any source including, but not limited to, blood, blood products, tissue, ascites, culture media, body fluids, skin, pus, uro-genital specimens, feces, foodstuffs, beverages, cosmetic products, pharmaceutical products, healthcare products, surfaces such as floors and tables, and airborne particles such as pollen and dust. The sample will be one that is suspected of having microorganisms. The sample may already have been tested for the presence of microorganisms and have tested positive for microorganisms. The sample will require the addition of a medium prior to step (a) if it does not include any medium and the medium is preferably a growth medium. The sample will require the addition of an adsorbent prior to step (a) if it does not include any adsorbent. The amount of medium and/or adsorbent to add to the sample will be dependent upon the estimated number of microorganisms in the sample and could easily be ascertained by one skilled in the art.

Plasma, serum, blood or a blood component is preferably mixed with the sample and the first solution in step (b). If plasma, serum, blood or a blood component is mixed with the sample and the first solution, the bulk of the plasma, serum, blood or a blood component is separated along with the medium and the bulk of the first solution from the adsorbent and the microorganisms and removed from the vessel during step (c). The sample, though, may be obtained from a source such as blood, blood products, tissue, body fluids, skin, pus, etc., and therefore already include plasma, serum, blood or a blood component. In such instances, the bulk of the plasma, serum, blood or a blood component is separated along with the medium and the bulk of the first solution from the adsorbent and the microorganisms during step (c).

The sample as provided in step (a) is suspended and this can be accomplished ) by gently shaking the container or vessel containing the sample. Step (b) provides that the sample and first solution are mixed in a vessel and this can be accomplished by briefly vortexing the vessel. The vessel is preferably a conical tube.

The adsorbent is selected from the group consisting of aluminum oxide, colloidal native hydrated aluminum silicates, crystalline hydrated alkali-aluminum silicates, silica, siliceous frustules, fragments of various species of diatoms, amorphous carbon, ion exchange resins, polymeric resin adsorbents, polystyrene resin cross-linked with divinyl benzene, activated charcoal, charcoal bound to fibers, fuller's earth bound to fibers, charcoal bound to fuller's earth and combinations thereof. Preferably, the adsorbent comprises activated charcoal.

The amount of sample that can be mixed with the first solution in step (b) is from about 0.1 mL to about 10 mL. Preferably, the amount of sample mixed with the first solution in step (b) is about 2 mL.

The amount of the first solution that can be mixed with the sample in step (b) is from about 0.1 to about 10 mL. The first solution preferably comprises an alkaline reagent. Alkaline reagents that can be used include, but are not limited to, ethanolamine, tri-sodium phosphate, sodium hydroxide and potassium hydroxide. The first solution can also comprise a detergent. Most preferably, the first solution comprises an alkaline reagent, a detergent and a chelating agent. Detergents that can be used with the present invention include, but are not limited to, cholic acid, deoxycholic acid, digitonin, n-dodecyl-.beta.-D-maltoside, glycodeoxycholic acid, n-lauroylsarcosine, Triton X-100, lauryl sulfate, saponin, polyoxyethylene sorbitan monooleate, polyethylene glycol P-1,1,3,3-tetramethylbutylphenyl ether and polyoxyethylene derivatives of fatty acids. Chelating agents that can be used with the present invention include, but are not limited to, EGTA and EDTA.

In a preferred embodiment, the first solution comprises sodium hydroxide, Triton X-100 and EDTA. More particularly, the first solution comprises 0.2 N sodium hydroxide, 1.0% Triton X-100 and 1 mM EDTA. The amount of first solution that can be mixed with this sample in step (b) is from about 0.1 mL to about 10 mL. Preferably, the amount of this first solution mixed with the sample in step (b) is about 2 mL.

The above method provides for separating the adsorbent and the microorganisms from the medium and the bulk of the first solution and removing the medium and the bulk of the first solution from the vessel. Preferably, the adsorbent and the microorganisms can be separated from the medium and the bulk of the first solution by centrifugation or filtration. Most preferably, the adsorbent and the microorganisms are separated from the medium and the bulk of the first solution by centrifugation for ten (10) minutes at $\geq$1,000 G to pellet the adsorbent and the microorganisms. Preferably, the medium is a growth medium.

Step (d) of the above method provides for adding a second solution to the vessel to resuspend the adsorbent and the microorganisms. After the second solution is added to the vessel, the vessel should be vortexed.

The amount of the second solution that can be added to the vessel in step (d) is from about 0.05 mL to about 5 mL. Preferably, the second solution comprises an acidic solution and/or a buffer such as Tris, HEPES, MOPS and phosphate. Buffers that can be used with the present invention have a pKa in the range of from about 5.0 to about 9.0. More preferably, buffers that can be used with the present invention have a pKa in the range of from about 6.0 to about 8.0.

Preferably, the second solution comprises a detergent and/or a salt. Detergents that can be used with the present invention include, but are not limited to, cholic acid, deoxycholic acid, digitonin, n-dodecyl-.beta.-D-maltoside, glycodeoxycholic acid, n-lauroylsarcosine, Triton X-100, lauryl sulfate, saponin, polyoxyethylene sorbitan monooleate, polyethylene glycol P-1,1,3,3-tetramethylbutylphenyl ether and polyoxyethylene derivatives of fatty acids. Salts that can be used with present invention include, but are not limited to, potassium chloride, sodium chloride, magnesium chloride, magnesium sulfate and calcium chloride.

In a preferred embodiment, the second solution comprises Tris, sodium chloride and Tween 80. More particularly, the second solution comprises 0.1 M Tris (pH 7.2), 0.15 M sodium chloride and 0.5% Tween 80. The amount of this second solution that can be added to the vessel in step (d) is from about 0.05 mL to about 5 mL. Preferably, the amount of this second solution added to the vessel in step (d) is about 1.0 mL.

Step (e) of the above method provides for detecting agglutination of the adsorbent which signifies bacterial pathogens are present in the sample. This can be accomplished in several ways such as light scattering methods, sedimentation methods, gently tilting the vessel and examining the vessel for clumping of the adsorbent, placing a drop of the suspension onto a glass slide and rocking the slide for up to 15 seconds or mixing it with a disposable loop, or placing 25 to 50 µL of the suspension onto a latex test card circle and mixing it with a disposable loop. Rapid, visible agglutination of the adsorbent is presumptive positive identification of bacterial pathogens.

The present invention also provides a method for detecting *Staphylococcus aureus* in a sample. This method comprises the steps of:

(a) suspending a sample comprising a medium and microorganisms, the microorganisms suspected of comprising *Staphylococcus aureus*;

(b) mixing the sample, an adsorbent and a first solution in a vessel;

(c) separating the adsorbent and the microorganisms from the medium and the bulk of the first solution and removing the medium and the bulk of the first solution from the vessel;

(d) adding a second solution to the vessel to resuspend the adsorbent and the microorganisms; and (e) detecting agglutination of the adsorbent wherein the agglutination of the adsorbent signifies *Staphylococcus aureus* is present in the sample.

Preferably, plasma, serum, blood or a blood component is mixed with the sample, the adsorbent and the first solution in step (b). If plasma, serum, blood or a blood component is mixed with the sample, the adsorbent and the first solution, the bulk of the plasma, serum, blood or a blood component is separated along with the medium and the bulk of the first solution from the adsorbent and the microorganisms and removed from the vessel during step (c). The sample, though, may be obtained from a source such as blood, blood products, tissue, body fluids, skin, pus, etc., and therefore already include plasma, serum, blood or a blood component. In such instances, the bulk of the plasma, serum, blood or a blood component is separated along with the medium and the bulk of the first solution from the adsorbent and the microorganisms during step (c).

Any of the aforementioned adsorbents can be used with this method although it is preferable that the adsorbent comprises activated charcoal.

The present invention also provides for another method for detecting *Staphylococcus aureus* in a sample. This method comprises the steps of:

(a) suspending a sample comprising a medium, an adsorbent and microorganisms, the microorganisms suspected of comprising *Staphylococcus aureus*;

(b) mixing the sample and a first solution in a vessel;

(c) separating the adsorbent and the microorganisms from the medium and the bulk of the first solution and removing the medium and the bulk of the first solution from the vessel;

(d) adding a second solution to the vessel to resuspend the adsorbent and the microorganisms; and (e) detecting agglutination of the adsorbent wherein the agglutination of the adsorbent signifies *Staphylococcus aureus* is present in the sample.

Preferably, plasma, serum, blood or a blood component is mixed with the sample and the first solution in step (b). If plasma, serum, blood or a blood component is mixed with the sample and the first solution, the bulk of the plasma, serum, blood or a blood component is separated along with the medium and the bulk of the first solution from the adsorbent and the microorganisms and removed from the vessel during step (c). The sample, though, may be obtained from a source such as blood, blood products, tissue, body fluids, skin, pus, etc., and therefore already include plasma, serum, blood or a blood component. In such instances, the bulk of the plasma, serum, blood or a blood component is separated along with the medium and the bulk of the first solution from the adsorbent and the microorganisms during step (c).

Any of the aforementioned adsorbents can be used with this method although it is preferable that the adsorbent comprises activated charcoal.

The samples used in the methods for detecting bacterial pathogens according to the present invention can be obtained from any source including, but not limited to, blood, blood products, tissue, ascites, culture media, body fluids, skin, pus, uro-genital specimens and feces. Samples may also be obtained for detection from foodstuffs and beverages; from cosmetic, pharmaceutical and healthcare products; from surfaces such as floors, tables, and the like; and from airborne particles, such as pollen and dust.

The term "adsorbent" as used in the methods of the present invention is preferably selected from the group provided above, however, for the purposes of this application, the term "adsorbent" includes all adsorbent materials that neutralize, bind, and inhibit antimicrobial substances. These adsorbents include resins as defined in U.S. Pat. No. 4,632,902, and non-resinous adsorbents.

The term "resin" as used herein is a subclass of adsorbents, and is further defined to include naturally occurring and synthetic resins, for example, ion exchange resins, non-functional polymeric resin adsorbents and, in particular, polystyrene resins cross-linked with divinyl benzene.

"Non-resinous adsorbents" as used herein are another subclass of adsorbents and are defined as naturally occurring and synthetic non-resin adsorbents and molecular sieves that can be used for clarifying, deodorizing, decolorizing, and filtering. Some of these non-resinous adsorbents are the same as those used during the production of antibiotics to remove antibiotics from culture medium growing antibiotic-producing bacteria.

These non-resinous adsorbents include various forms of 1) aluminum oxide (alumina), 2) colloidal native hydrated aluminum silicates (clays), such as bentonite, kaolin, and fuller's earth, 3) crystalline hydrated alkali-aluminum silicates (sodium or calcium zeolites), 4) silica (silica gel, silica beads) such as Davisil, 5) siliceous frustules and fragments of various species of diatoms (infusorial earth, diatomaceous earth) such as Celite® (Manville Products Corporation, Denver, Colo., USA) and 6) amorphous carbon (in particular, activated carbon) such as Carboraffin, Norite® (American Norit Company Inc., Jacksonville, Fla., USA), Opocerbyl and Ultracarbon. Naturally occurring adsorbent activated charcoal, which has been used to prevent the lethal effects of oxidation in transport media and growth media, can also be used. This media has been used for the transport of fastidious organisms such as *Neisseria gonorrhoeae* and the cultivation of *Legionella* species. Non-resinous adsorbents do not require pre-treatment with a surfactant in order to function. Treatment with surfactants may even decrease the adsorbtive capabilities of these materials.

Many of these non-resinous adsorbents remove antimicrobial substances in culture. Preferred non-resinous adsorbents are the colloidal native hydrated aluminum silicates (clay) and the amorphous carbon (activated carbon) groups of adsorbent materials. Additionally preferred materials are fuller's earth or activated charcoal used singularly or in combination.

The samples used in the methods for detecting bacterial pathogens according to the present invention contain media formulated to be useful with the adsorbent. Preferably, the media is growth media and the growth media can include general purpose media such as tryptic soy broth, brain heart infusion broth, Columbia broth and Brucella broth.

Suitable surfactants or absorption enhancers can be included in the first and second solutions as briefly described above. Other suitable surfactants or absorption enhancers that can be used in the dissociation (first solution) and/or second solutions include, for example, oleic acid, polyoxyethylene derivatives of fatty acids, partial esters of sorbitol anhydride, such as for example, Tween 20, polyoxyl 40 stearate, polyoxyethylene 50 stearate, fusieates, bile salts, octoxynol and combinations thereof. Suitable surfactants include non-ionic, anionic and cationic surfactants.

EXAMPLES

The present invention is further detailed in the following Examples which are offered by way of illustration and are not intended to limit the invention in any manner. Standard techniques well known in the art or the techniques specifically described below are utilized.

Example 1

Plastic BacT/ALERT FA culture bottles (bioMerieux, Inc.) were inoculated with 10 mL of normal human blood and one of forty (40) *Staphylococcal* isolates (19 *S. aureus*, 19 *S. epidermidis*, 1 *S. capitis* and 1 *S. warneri*) and one of fifteen (15) non-*Staphylococcal* isolates (5 *S. pneumoniae*, 5 *S. pyrogenes* and 5 *E. faecalis*). Test strains were identified using a VITEK 2 instrument (bioMerieux, Inc.). Broth samples from positive FA bottles were mixed with an equal volume of a first solution (Solution A) and centrifuged to pellet microorganisms and charcoal. The pellet was resuspended in a small volume of a second solution (Solution B). One drop of the resulting charcoal-microorganism "slurry" was spread onto a reader card well and rocked for up to five (5) to fifteen (15) seconds. The observance of large charcoal aggregates correlated with the presence of *S. aureus* in the broth sample. A more detailed description of the method is as follows:

1. Shake the positive bottle gently to resuspend charcoal.
2. Add 2 mL of sample to 2 mL of Solution A in a conical tube.
3. Mix the tube contents and centrifuge for 10 min at ≧1,000G to pellet the microorganisms and charcoal.
4. Remove all of the supernatant.
5. Thoroughly resuspend the charcoal-bacterial pellet in 1.0 mL of Solution B by vortexing the tube.
6. Gently tilt the capped tube and examine for clumping of charcoal, OR place 1 drop onto a glass slide and rock for up to 5-15 seconds, or mix with a disposable loop, OR place 25-50 µL onto a latex test card circle and mix with a disposable loop. Rapid, visible agglutination of the charcoal is presumptive positive for *S. aureus*.

Solution A included 0.2N NaOH, 1.0% Triton X-100 and 1 mM EDTA and Solution B included 0.1M Tris pH 7.2, 0.15M NaCl and 0.5% Tween 80. Other highly basic compounds such as ethanolamine, potassium hydroxide and tri-sodium phosphate can be substituted for sodium hydroxide. The results of this experiment are shown below in TABLE 1.

TABLE 1

| Organism | Test Strain | Rapid Staph Assay Results |
|---|---|---|
| S. aureus | ATCC 29213 | 2+ |
| S. aureus | ATCC 25923 | 3+ |
| S. aureus | ATCC 43300 | 3+ |
| S. aureus | ATCC 6538 | 4+ |
| S. aureus | ATCC 12600 | 4+ |
| S. aureus | BJ0242 | 2+ |
| S. aureus | BJ0159 | 2+ |
| S. aureus | UCLA 114 | 2+ |
| S. aureus | D14906 | 4+ |
| S. aureus | D14790 | 2+ |
| S. aureus | OTC 80 | 2+ |
| S. aureus | DUKE1 | 3+ |
| S. aureus | D15077 | 1+ |
| S. aureus | D14908 | 1+ |
| S. aureus | D14891 | 3+ |
| S. aureus | D14914 | 2+ |
| S. aureus | D15055 | 3+ |
| S. aureus | D15207 | 4+ |
| S. aureus | DUKE5 | 3+ |
| S. epidermidis | ATCC 14990 | no agglutination |
| S. epidermidis | ATCC 29997 | no agglutination |
| S. epidermidis | ATCC 49134 | no agglutination |
| S. epidermidis | ATCC 12228 | no agglutination |
| S. epidermidis | 71701B | no agglutination |
| S. epidermidis | 72401B | no agglatination |
| S. epidermidis | 7BE4727 | no agglutination |
| S. epidermidis | 72601B | no agglutination |
| S. epidermidis | 71601B | no agglutination |
| S. epidermidis | 71801B | no agglutination |
| S. epidermidis | 71901B | no agglutination |
| S. epidermidis | 72501B | no agglutination |
| S. epidermidis | 72101B | no agglutination |
| S. epidermidis | 72201B | no agglutination |
| S. epidermidis | 72001B | no agglutination |
| S. epidermidis | 72301B | no agglutination |
| S. epidermidis | 72701B | no agglutination |
| S. epidermidis | 155 | no agglutination |
| S. epidermidis | 73001B | no agglutination |
| S. capitis | 7BH6481 | no agglutination |
| S. warneri | 7BV9227 | no agglutination |
| S. pneumoniae | OTC 2 | no agglutination |
| S. pneumoniae | OTC 24 | no agglutination |
| S. pneumoniae | OTC 51 | no agglutination |
| S. pneumoniae | OTC 52 | no agglutination |
| S. pneumoniae | ATCC 33400 | no agglutination |
| E. faecalis | D14775 | 2+ |
| E. faecalis | D15263 | 2+ |
| E. faecalis | ATCC 29212 | 2+ |
| E. faecalis | ATCC 33186 | 3+ |
| E. faecalis | ATCC 33012 | 4+ |
| S. pyogenes | 14289 | no agglutination |
| S. pyogenes | 49117 | no agglutination |
| S. pyogenes | 49399 | no agglutination |
| S. pyogenes | OTC 53 | no agglutination |
| S. pyogenes | ATCC 19615 | no agglutination |

As is apparent from TABLE 1, aggregated charcoal or agglutination was observed with all S. aureus specimens processed with the novel solutions (n=19; 100% sensitivity). All Coagulase Negative Staphylococci (CNS) strains tested were negative (n=19; 100% specificity) and 10 of the 15 non-Staphylococcal gram-positive isolates were negative (86% specificity). The 5 non-Staphylococcal gram-positive isolates that were positive were E. faecalis isolates.

FIG. 1 shows the agglutination pattern for several of these isolates. In particular, Samples 1, 3, 5, 7, 9 and 11 were six of the S. aureus isolates from positive BacT/ALERT FA bottles and Samples 2, 4, 6, 8, 10 and 12 were six of the CNS isolates from positive BacT/ALERT FA bottles.

The method described and used in this experiment provides a rapid and inexpensive screening method or "spot test" for S. aureus recovered from positive charcoal-containing BacT/ALERT blood culture bottles. Apart from the two processing buffers, no additional reagents were required and the result is available in 15 minutes.

Example 2

Plastic BacT/ALERT SA culture bottles (bioMerieux, Inc.) were inoculated with 10 mL normal human blood and one of twelve Staphylococcal isolates (6 S. aureus, 4 S. epidermidis, 1 S. capitis and 1 S. warneri). Test strains were identified using a VITEK 2 instrument (bioMerieux, Inc.). Broth samples from positive SA bottles were mixed with activated charcoal and an equal volume of a first solution (Solution A), and then centrifuged to pellet microorganisms and charcoal. The pellet was resuspended in a small volume of a second solution (Solution B). One drop of the resulting charcoal-microorganism "slurry" was spread onto a reader card well and rocked for up to five (5) to fifteen (15) seconds. The observance of large charcoal aggregates correlated with the presence of S. aureus in the broth sample. A more detailed description of the method is as follows:

1. Shake the positive bottle gently to resuspend the microorganisms.
2. Add 0.5 mL of a sterile 6.5% w/v activated charcoal suspension to 2.5 mL of Solution A in a conical tube.
3. Add 2.5 mL of positive SA broth to the tube.
4. Mix tube contents, and centrifuge for 10 min at $\geq 1,000$ G to pellet microorganisms and charcoal.
5. Remove all of the supernatant.
6. Thoroughly resuspend the charcoal-bacterial pellet in 1.0 mL of Solution B by vortexing the tube.
7. Gently tilt the capped tube and examine for clumping of charcoal, OR place 1 drop onto a glass slide and rock for up to 5-15 seconds, or mix with a disposable loop, OR place 25-50 µL onto a latex test card circle and mix with a disposable loop. Rapid, visible agglutination of the charcoal is presumptive positive for S. aureus.

Solution A included 0.2N NaOH, 1.0% Triton X-100 and 1 mM EDTA and Solution B included 0.1M Tris pH 7.2, 0.15M NaCl and 0.5% Tween 80. Other highly basic compounds such as ethanolamine, potassium hydroxide and tri-sodium phospate can be substituted for sodium hydroxide. The results of this experiment are shown below in TABLE 2.

TABLE 2

| Isolate Designation | VITEK 2 Identification | Result (+/− aggregation) |
|---|---|---|
| BJ0159 | S. aureus | Aggregated charcoal (+) |
| ATCC 12600 | S. aureus | Aggregated charcoal (+) |
| ATCC 29213 | S. aureus | Aggregated charcoal (+) |
| ATCC 25923 | S. aureus | Aggregated charcoal (+) |
| ATCC 43300 | S. aureus | Aggregated charcoal (+) |
| ATCC 6538 | S. aureus | Aggregated charcoal (+) |
| ATCC 14990 | S. epidermidis | No aggregation (−) |
| ATCC 29997 | S. epidermidis | No aggregation (−) |
| ATCC 49134 | S. epidermidis | No aggregation (−) |
| ATCC 12228 | S. epidermidis | No aggregation (−) |
| 7BH6481 | S. capitis | No aggregation (−) |
| 7BV9227 | S. warneri | No aggregation (−) |

As is apparent from TABLE 2, aggregated charcoal was observed with all six of the S. aureus specimens processed with the novel solution and exogenous charcoal. All non-*S. aureus* strains tested did not cause charcoal aggregation.

The methods described herein provide a rapid, inexpensive and accurate means to identify bacterial pathogens such as *S. aureus* in samples. The method allows for detection or confirmation of bacterial pathogens such as *S. aureus* within 15 minutes.

Thus, while there have been described what are presently believed to be the preferred embodiments of the present invention, those skilled in the art will realize that other and further embodiments can be made without departing from the spirit and scope of the invention, and it is intended to include all such further modifications and changes as come within the true scope of the invention.

What is claimed is:

1. A method for detecting bacterial pathogens in a sample, comprising the steps of:
   (a) suspending a sample comprising a medium and microorganisms, said microorganisms suspected of comprising bacterial pathogens;
   (b) mixing said sample, an absorbent and a first solution in a vessel;
   (c) separating said absorbent and said microorganisms from said medium and a bulk of said first solution and removing said medium and the bulk of said first solution from said vessel;
   (d) adding a second solution to said vessel to resuspend said absorbent and said microorganisms; and
   (e) detecting agglutination of said absorbent wherein the agglutination of said absorbent signifies said bacterial pathogens are present in said sample;
   wherein said first solution comprises sodium hydroxide, polyethylene glycol tert-octylphenyl ether and EDTA, and said second solution comprises Tris, sodium chloride and polyoxyethylenesorbitan monooleate.

2. The method according to claim 1, wherein said bacterial pathogens comprise *Staphylococcus aureus*.

3. The method according to claim 1, wherein said bacterial pathogens comprise *Enterococcus faecalis*.

4. The method according to claim 1, wherein said absorbent is selected from the group consisting of aluminum oxide, colloidal native hydrated aluminum silicates, crystalline hydrated alkali-aluminum silicates, silica, siliceous frustules, fragments of various species of diatoms, amorphous carbon, ion exchange resins, polymeric resin absorbents, polystyrene resin cross-linked with divinyl benzene, activated charcoal, charcoal bound to fibers, fuller's earth bound to fibers, charcoal bound to fuller's earth and combinations thereof.

5. The method according to claim 1, wherein from about 5 to about 150 mg of said absorbent is mixed with said sample and said first solution in step (b).

6. The method according to claim 1, wherein from about 0.1 to about 10 mL of said sample is mixed with said absorbent and said first solution in step (b).

7. The method according to claim 1, wherein from about 0.1 to about 10 mL of said first solution is mixed with said sample and said absorbent in step (b).

8. The method according to claim 1, wherein plasma, serum, blood or a blood component is mixed with said sample, said absorbent and said first solution in step (b).

9. A method for detecting bacterial pathogens in a sample, comprising the steps of:
   (a) suspending a sample comprising a medium, an absorbent and microorganisms, said microorganisms suspected of comprising bacterial pathogens;
   (b) mixing said sample and a first solution in a vessel;
   (c) separating said absorbent and said microorganisms from said medium and a bulk of said first solution and removing said medium and the bulk of said first solution from said vessel;
   (d) adding a second solution to said vessel to resuspend said absorbent and said microorganisms; and
   (e) detecting agglutination of said absorbent wherein the agglutination of said absorbent signifies said bacterial pathogens are present in said sample;
   wherein said first solution comprises sodium hydroxide, polyethylene glycol tert-octylphenyl ether and EDTA, and said second solution comprises Tris, sodium chloride and polyoxyethylenesorbitan monooleate).

10. The method according to claim 9, wherein said bacterial pathogens comprise *Staphylococcus aureus*.

11. The method according to claim 9, wherein said bacterial pathogens comprise *Enterococcus faecalis*.

12. The method according to claim 9, wherein said absorbent is selected from the group consisting of aluminum oxide, colloidal native hydrated aluminum silicates, crystalline hydrated alkali-aluminum silicates, silica, siliceous frustules, fragments of various species of diatoms, amorphous carbon, ion exchange resins, polymeric resin absorbents, polystyrene resin cross-linked with divinyl benzene, activated charcoal, charcoal bound to fibers, fuller's earth bound to fibers, charcoal bound to fuller's earth and combinations thereof.

13. The method according to claim 9, wherein from about 0.1 to about 10 mL of said sample is mixed with said first solution in step (b).

14. The method according to claim 9, wherein from about 0.1 to about 10 mL of said first solution is mixed with said sample in step (b).

15. The method according to claim 9, wherein plasma, serum, blood or a blood component is mixed with said sample and said first solution in step (b).

16. A method for detecting *Staphylococcus aureus* in a sample, comprising the steps of:
   (a) suspending a sample comprising a medium and microorganisms, said microorganisms suspected of comprising *Staphylococcus aureus*;
   (b) mixing said sample, an absorbent and a first solution in a vessel, said absorbent comprising activated charcoal;
   (c) separating said absorbent and said microorganisms from said medium and a bulk of said first solution and removing said medium and the bulk of said first solution from said vessel;
   (d) adding a second solution to said vessel to resuspend said absorbent and said microorganisms; and
   (e) detecting agglutination of said absorbent wherein the agglutination of said absorbent signifies *Staphylococcus aureus* is present in said sample;
   wherein plasma, serum, blood or blood component is mixed with said sample, said absorbent and said first solution in step (b) and separated and removed from said vessel in step (c) with said medium and the bulk of said first solution, and
   wherein said first solution comprises sodium hydroxide, polyethylene glycol tert-octylphenyl ether and EDTA, and said second solution comprises Tris, sodium chloride and polyoxyethylenesorbitan monooleate).

17. A method for detecting *Staphylococcus aureus* in a sample, comprising the steps of:
   (a) suspending a sample comprising a medium, and absorbent and microorganisms, said microorganisms suspected of comprising *Staphylococcus aureus* and said absorbent comprising activated charcoal;
   (b) mixing said sample and a first solution in a vessel;

(c) separating said absorbent and said microorganisms from said medium and a bulk of said first solution and removing said medium and the bulk of said first solution from said vessel;

(d) adding a second solution to said vessel to resuspend said absorbent and said microorganisms; and (e) detecting agglutination of said absorbent wherein the agglutination of said absorbent signifies *Staphylococcus aureus* is present in said sample;

wherein plasma, serum, blood or blood component is mixed with said sample and said first solution in step (b) and separated and removed from said vessel in step (c) with said medium and the bulk of said first solution, and wherein said first solution comprises sodium hydroxide, polyethylene glycol tert-octylphenyl ether and EDTA, and said second solution comprises Tris, sodium chloride and polyoxyethylenesorbitan monooleate).

* * * * *